United States Patent [19]
Fink et al.

[11] Patent Number: 5,808,918
[45] Date of Patent: Sep. 15, 1998

[54] HIERARCHICAL BIOLOGICAL MODELLING SYSTEM AND METHOD

[75] Inventors: Pamela K. Fink; Kenneth S. Kornman, both of San Antonio, Tex.

[73] Assignee: Medical Science Systems, Inc., Newport Beach, Calif.

[21] Appl. No.: 882,597

[22] Filed: Jun. 25, 1997

Related U.S. Application Data

[63] Continuation of Ser. No. 422,175, Apr. 14, 1995, Pat. No. 5,657,255.

[51] Int. Cl.[6] ................................................. G06G 7/48
[52] U.S. Cl. ............................................ 364/578; 364/496
[58] Field of Search ..................................... 364/578, 496, 364/554, 499, 500; 707/3; 395/920

[56] References Cited

U.S. PATENT DOCUMENTS

| | | | |
|---|---|---|---|
| 3,800,288 | 3/1974 | Russell et al. | 340/172.5 |
| 4,881,175 | 11/1989 | Ladner | 364/496 |
| 5,005,143 | 4/1991 | Altschuler et al. | 364/554 |
| 5,081,584 | 1/1992 | Omichinski et al. | 364/497 |
| 5,307,287 | 4/1994 | Cramer, III et al. | 364/496 |
| 5,331,573 | 7/1994 | Balaji et al. | 364/500 |
| 5,418,944 | 5/1995 | DiPace et al. | 395/600 |
| 5,424,963 | 6/1995 | Turner et al. | 364/578 |
| 5,434,796 | 7/1995 | Weininger | 364/496 |
| 5,463,564 | 10/1995 | Agrafiotis et al. | 364/497 |
| 5,495,423 | 2/1996 | DeLisi et al. | 364/496 |
| 5,526,281 | 6/1996 | Chapman et al. | 364/496 |
| 5,657,255 | 8/1997 | Fink et al. | 364/578 |

OTHER PUBLICATIONS

Fishwick, P.A., "A Study of Terminology and Issues in Qualitative Simulation", Department of Computer and Information Sciences University of Florida, pp. 5–9 Jan., 1989.

Fishwick P. A., "Qualitative methodology in simulation model engineering", Simulation vol. 52, No. 3, pp. 95–101, Mar. 1989.

Forbus, K. D., "Qualitative Process Theory", Artificial Intelligence, vol. 24, pp. 85–168, 1984.

Hamscher, W., Console, L. and de Kleer, J., "Readings in Model–based Diagnosis", Chapter 1, pp. 1–2, 1992.

Hoang, K. T., "Physiologically based pharmacokinetic models: mathematical fundamentals and simulation implementations", Toxicology Letters, vol. 79, pp. 99–106, Sep., 1995.

International Journal of Man–Machine Studies "Editorial: Developments in Expert Systems", vol. 19, pp. 399–402, 1983.

Karp, P. D. and Friedland, P., "Coordinating the Use of Qualitative and Quantitative Knowledge in Declarative Device Modeling", Artificial Intelligence, Simulation, and Modeling, Chapter 7–8, pp. 189–207.

Kuipers, B., "Qualitative Simulation", Aartificial Intelligence, vol. 29, pp. 289–388, 1986.

Patil, R. S., Szolovits, P. and Schwartz, W. B., "Causal Understanding of Patient Illness in Medical Diagnosis", IJCAI, pp. 893–899, 1981.

(List continued on next page.)

*Primary Examiner*—Kevin J. Teska
*Assistant Examiner*—Tyrone V. Walker
*Attorney, Agent, or Firm*—Fenwick & West LLP

[57] ABSTRACT

A hierarchical biological modelling system and method provides integrated levels of information synthesized from multiple sources. An executable model of a biological system is developed from information and structures based on the multiple sources. The model is balanced to ensure that it matches the information and structures. Once the model is created and balanced it can be used to provide insight into phenomena at the cellular, or subcellular level, as well as phenomena at the patient, organ and system levels. From this information clinical trials can be emulated, biologic targets for drug development can be identified and subcellular phenomena over time can be observed. The model provides an integrated view of a multi-variable biological system.

5 Claims, 9 Drawing Sheets

OTHER PUBLICATIONS

Pedley, T.J., Corieri, P., Kamm, R. D., Grotberg, J. B., Hydon, P. E. and Schroter, R. C., "Gas flow and mixing in the airways", Critical Care Medicine, vol. 22, No. 9, pp. S24–S36, Sep., 1994.

Sieburg, H. B. and Müller–Sieburg, C., "the CyberMensch Simulation Server for the Planning of Clinical Trials", Interactive Technology and the New Paradigm for Healthcare, Chapter 65, pp. 445–454, 1995.

Sieburg, H. B., "In Silico Environments Augment Clinical Trials", 4527 IEEE Engineering in Medicine and Biology, vol. 15, No. 2, pp. 47–59, Mar./Apr., 1996.

Sieburg, H. B., "Methods in the Virtual Wetlab I: Rule–based reasoning driven by nearest–neighbor lattice dynamics", Artificial Intelligence in Medicine, vol. 6, No. 4, pp. 301–319, Aug., 1994.

Uckun, W., "Model–Based Reasoning In Biomedicine", Critical Reviews in Biomedical Engineering, vol. 19(4), pp. 261–292, 1992.

Weld, D. S. and de Kleer, J., "Readings in Qualitative Reasoning About Physical Systems", pp. 1–10, 1990.

Davis, R., "Reasoning from first principles in electronic troubleshooting", International Journal of Man–Machine Studies, vol. 19, pp. 403–423, 1983.

De Kleer, J. and Brown, J. S., "A Qualitative Physics Based on Confluences", Artificial Intelligence, vol. 24, pp. 7–83, 1984.

Fink, P. K. and Lusth, J. C., "Expert Systems and Diagnostic Expertise in the Mechanical and Electrical Domains", IEEE Transactions on Systems, Man, and Cybernetics, vol. SMC–17, No. 3, pp. 340–349, May/Jun. 1987.

Cellier, F. E., "Qualitative Modeling and Simulation: Promise or Illusion", Proceedings of the 1991 Winter Simulation Conference, pp. 1086–1090, 1991.

Clancey, W. J., "Viewing Knowledge Bases as Qualitative Models", IEEE Expert, Tools and Techniques, pp. 9–23, Summer 1989.

Conolly, R. B. and Kimbell, J. S., "Computer Simulation of Cell Growth Governed by Stochastic Processes: Application to Clonal Growth Cancer Models", Toxicology and Applied Pharmacology, vol. 124, pp. 284–295, 1994.

Aliev, M.K. and Saks, V.A., "Mathematical modeling of intracellular transport processes and the creatine kinase systems: a probability approach. [Review]", Molecular & Cellular Biochemistry, vol. 133–134, pp. 333–346, Apr.–May, 1994.

Barr, A., Cohen, P. R. and Feigenbaum, E. A., "Knowledge–based Simulation, Alfred Round—Intelligent Interfaces", The Handbook of Artificial Intelligence, vol. 4, Charpter 22, pp. 7–15, Dec. 1989.

Celada, F. and seiden, P. E., "A computer model of cellular interactions in the immune system", Immunology Today, vol. 13 No. 2, pp. 56–62, 1992.

HIERARCHICAL BIOLOGICAL MODELLING SYSTEM AND METHOD

RELATED APPLICATIONS

This is a continuation of application Ser. No. 08/422,175, filed on Apr. 14, 1995, now U.S. Pat. No. 5,657,255.

COPYRIGHT NOTIFICATION

Portions of this patent application contain materials that are subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to modelling, and in particular a dynamic interactive modelling system which models biological systems from the cellular, or subcellular level, to the human or patient population level.

BACKGROUND OF THE INVENTION

New drug development is typically motivated by the need or opportunity to affect an individual's quality of life. Development focuses on identifying and selecting compounds having the potential to affect one or more mechanisms thought to be critical in altering specific clinical aspects of the disease processes.

Drug development is also motivated by exciting research data regarding cellular and subcellular phenomena. Very often, however, the data considers only an isolated and rather narrow view of an entire system. Such data may not provide an integrated view of the complete biological system. Moreover, the narrow findings reported are not always entirely accurate when translated to the whole body level.

Current methods of obtaining data for biological processes require extremely time consuming laboratory experiments that lead to animal experiments and clinical trials. From these trials and experiments, data are obtained which usually focus on a very narrow part of the biological system. While conclusions may be drawn by assimilating experimental data and published information, it is difficult, if not impossible, to synthesize the relationships among all the available data and knowledge. In fact, the human mind is only capable of considering approximately seven factors at one time, and lacks the ability to accurately account for feedback in systems over time. Furthermore, incorporation of multiple uncertainties, as well as feedback, often leads to oversimplification or artificial partitioning by the human mind, which can result in misleading conclusions.

Previous modelling efforts for designing drugs have typically focused on creating molecular models of a proposed drug or drug target. The molecular models are designed to meet certain criteria believed to have a desired impact at the molecular level. The desired impact is generally determined by studying the biology of interest at the molecular level through laboratory experiments.

Drugs designed using this type of modelling either represent refinements of existing drugs or an attempt to develop a drug for a new part of the disease that was suggested from conclusions drawn from clinical trials and laboratory experiments. The complexity of the information, however, does not always provide a clear and consistent picture from which accurate conclusions can be drawn, and the resulting designer drugs often reflect this inaccuracy.

Typically, designer drugs often meet design goals related to particular conclusions and observations at a cellular or subcellular level, but may fail when clinically tested because the design process fails to take into account the nuances of the complete biological system. Only after numerous costly trial-and-error clinical trials, and constant redesigning of the clinical use of the drug to account for lessons learned from the most recent clinical trial, is a drug having adequate safety and efficacy finally realized. This process of clinical trial design and redesign, multiple clinical trials and, in some situations, multiple drug redesigns requires great expense of time and money. Even then, the effort may not produce a marketable drug.

This scenario has a chilling effect on efforts to produce a drug for anything but an extremely large segment of the population. Biological abnormalities which may be treatable by a drug may not explored because the potential market for the drug does not justify the expenditure of resources necessary to design, test, and obtain approval for the drug.

Because of the high initial costs of clinical trials, experimentation, and government approval, drug development today focuses on large patient populations. Even then, development is extremely speculative. In summary, the overhead for drug development is very high, and difficult to justify except for the largest of patient populations.

Clinical trials typically are designed to isolate on a single variable, and use a placebo control group as a baseline from which the variable is measured. Observations from a clinical trial attempt to draw conclusions from apparent differences between the control group and the experimental group. These observations, however, do not take into account the multi-variable dynamic nature of the patients individually, or as a group. Such variations usually increase the variability in the data and require large test populations to deal with the variability in an appropriate statistical manner.

A typical cycle for a clinical trial can require years; designing the trial may take six months, performance of the trial may take a year, and analysis of the results may take yet another six months. After years of testing, the results still may be subject to suspicion. Additionally, a trial may be one of several ongoing trials necessary to address the variables associated with a particular area of investigation.

Due to the single-variable nature of the drug development business, the reported data results in a great degree of uncertainty. Each study provides a very narrow, often debatable, view of the complete system. Ultimately, the different studies fail to provide a complete picture of the entire biological system, since the studies develop information from different perspectives and assumptions.

What is needed then, is an alternative system and method which efficiently discovers and conveys information regarding complex biological systems.

SUMMARY OF THE INVENTION

It is therefore an object of the present invention to provide a system and method for modelling biological systems and disease processes.

It is another object of the present invention to provide a system and method for modelling biological systems in a manner reflecting the dynamic and multi-variable nature of the systems.

It is still another object of the present invention to provide a system and method for representing a biological system in a hierarchical manner of varying levels of complexity.

It is yet another object of the present invention to provide a hierarchical modelling system which is interactive.

It is a further object of the present invention to provide a method for drug development which relies upon the present modelling method and system.

Another object of the present invention is the provision of a method for developing clinical trial designs through the application of the present modelling method and system.

These objects are achieved by the present dynamic computer-based system that simulates interrelated biological findings and hypotheses at the cellular and subcellular levels to better predict and successfully alter clinical outcomes manifested as signs and symptoms of disease. The present invention provides an interactive tool to help identify new drug targets, to develop a better understanding of key biological mechanisms, and to assess the potential for influencing important clinical outcomes. The functional computer model integrates all of the biologic relationships that are known to exist and that are relevant to the particular disease process of interest. The integration provides a dynamic executable model reflecting changes over time at each level of the system hierarchy. For example, the course of a particular disease progression, and impact of a particular treatment on the progression, are demonstrable by the system.

The present system and method recognize that the body is organized in levels of increasing complexity from the subcellular level to the cellular level to the tissue/organ systems to the whole external body of an intact animal. At every level, interrelated and redundant mechanisms with complex feedback loops produce responses that influence the clinical outcomes. Many of these mechanisms are modified in individual patients by genetic and environmental factors.

As mentioned above, current drug development is typically the result of new, exciting observations at the cellular and subcellular level. The present invention realizes that although these observations identify potential targets for new drug discovery, the targeted mechanisms are rarely independent. A change in one system can have cascading effects due to complex interrelationships at higher levels of complexity that will determine drug efficacy, side effects, and drug development profiles.

Other objects and advantages of the present invention will become apparent from the following detailed description, which when viewed in conjunction with the accompanying drawings, sets forth the preferred embodiment of the invention.

DETAILED DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for teaching one skilled in the art how to make and/or use the invention.

The present invention provides a method and apparatus which allows critical integrated evaluation of conflicting data and alternative hypotheses. A model is developed representing not just chemical processes at the lowest level, but the larger biological systems impacting on these chemical processes. This provides a multi-variable view of the system, as opposed to the old single variable system. The present invention also provides cross-disciplinary observations through synthesis of information from two or more disciplines into a single model, or through linking two models which respectively represent different disciplines.

The model can be built to simulate individual patients or specific groupings of patients, and not the general population as a whole. By providing individual patient simulations, individual susceptibility and environmental factors can be directly linked to the biology and clinical outcomes. Specific grouping patient simulations also provides a way of exploring patterns of patient-level factors that may influence biologic behavior. The model also incorporates critical anatomic considerations which are relevant to the biological area or system of interest. By assessing localization of specific mechanisms associated with the anatomy, certain constraints on biological interactions are revealed.

Figure 3:
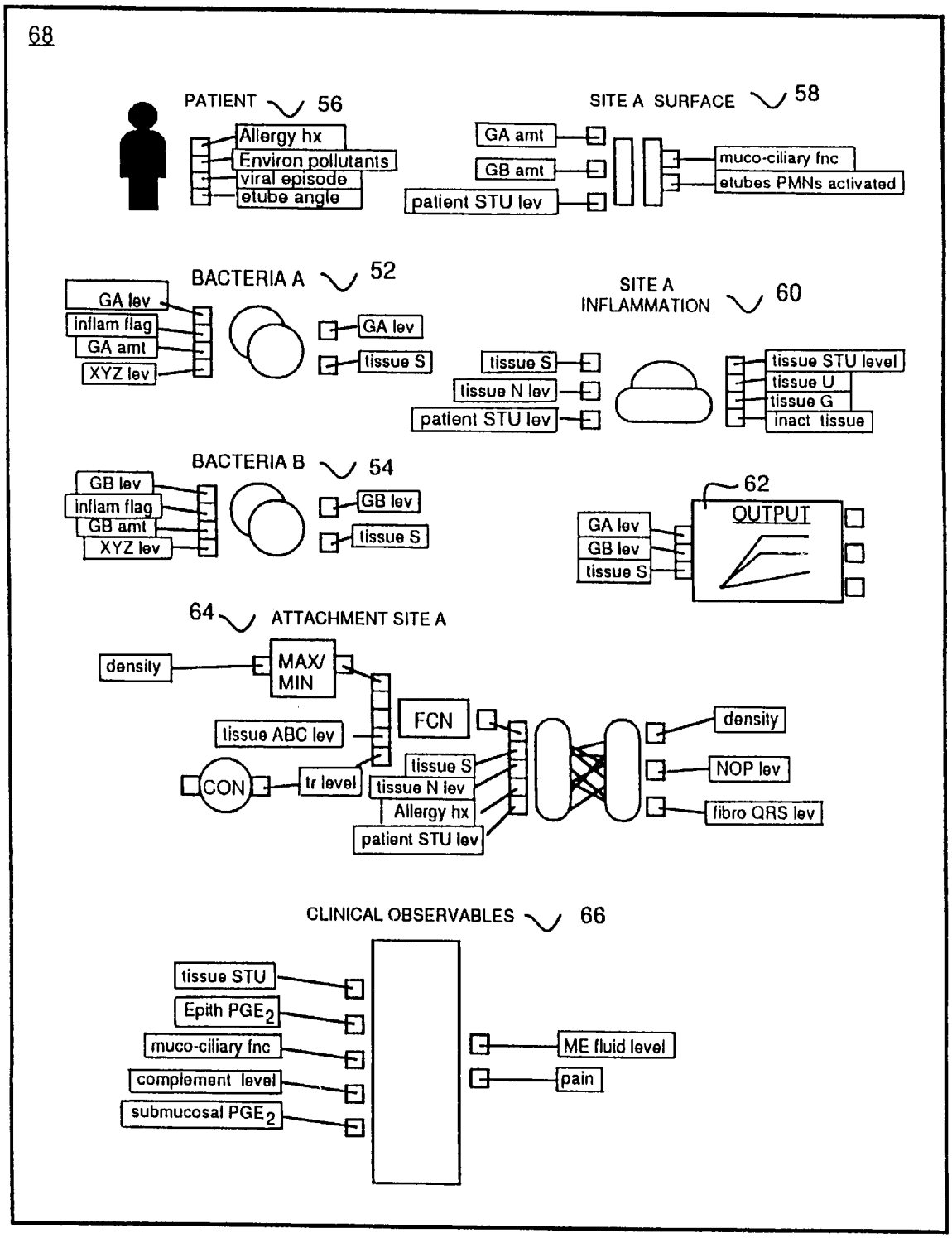
FIG. 3 is a block diagram showing the typical display and structure of a low level of the model.

The model is hierarchical, and reflects the particular system and anatomical factors relevant to the issues to be explored by the model. The level of detail at which the hierarchy starts, and the level of detail at which the hierarchy ends, are largely dictated by the particular intended use of the model. Because drugs often operate at the subcellular level, the lowest level of the hierarchy will often be the subcellular level. And because the individual is the most common entity of interest with respect to the safety and efficacy of the drug, the individual in the form of clinical observables is often represented at the highest level of the hierarchy, as depicted in FIG. 3, element 66.

Within each level of the hierarchy there are fundamental model units (FMU) which represent relevant biological information and processes at that particular level. An FMU typically reflects a particular relationship among several factors affecting the level. Any one level is typically comprised of multiple FMUs, which may be linked together. The levels, in turn, are linked together so that data and information developed at one level are passed on to other levels in accordance with the model.

Figure 1:
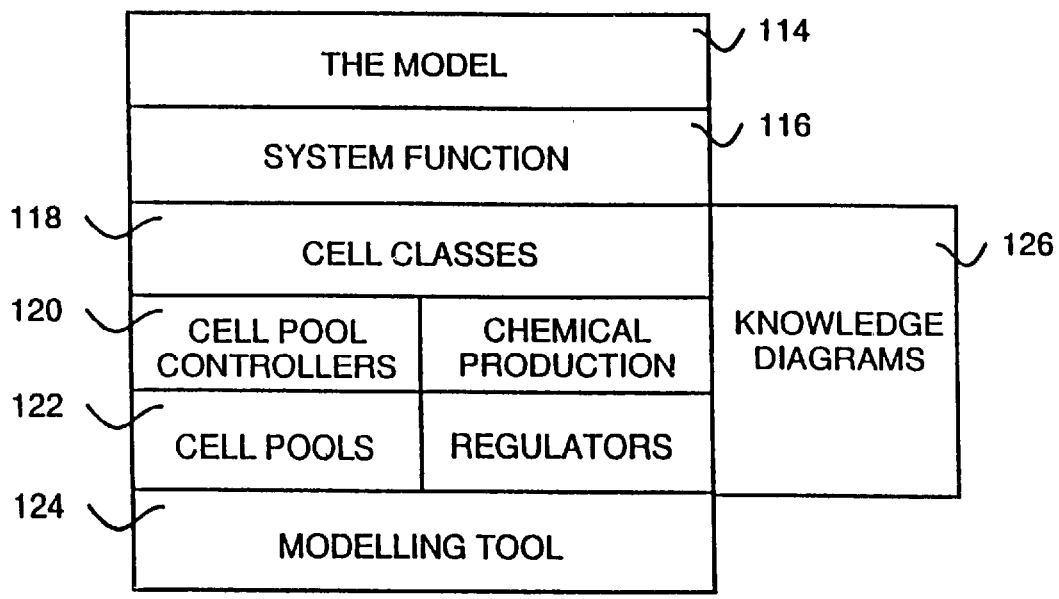
FIG. 1 is a block diagram showing an example of a software hierarchy which could be used as a basis for model creation.

FIG. 1 is a block diagram showing an example of a software hierarchy which could be used as a basis for model creation. The lowest level is the basic model development tool 124, such as EXTEND™ by Imagine That!

According to the disclosed embodiment, a second level 122 includes cell pools and regulators. A cell pool is a population of cells of a particular type or which is in a particular state. Regulators control inflow and outflow of a cell pool. The next level 120 is comprised of cell pool controllers and chemical production. A cell pool controller is a cell pool and its regulators (in the form of chemical levels in the environment of the cell pool).

The next level 118 is comprised of cell classes. A cell class is a group of related cell controllers, usually of a particular cell type but in different states, plus the chemicals that are produced by the various cell pools, and the chemicals that control the production.

It should be noted that levels 118, 120 and 122 are based on Knowledge Diagrams (KDs) described in greater detail below. Put another way, these levels implement the KDs which are developed in the preliminary stages of model design. This relationship is indicated by box 126.

The next level 116 represents system function, or system/body response/function, which is a collection of cell classes constituting a coordinated biological function, such as immune response or bone remodelling. Finally, level 114 represents the model which is the sum of the parts below. The model is a collection of system/body response/function representing key components of the biological processes (e.g., disease) of interest.

An example of the hierarchy could be cell pools and regulators at the lowest level, cell classes and chemical production at the next level, cell types at the next level, human/anatomical response at the next level, manifestation of the disease at the next level, and clinical signs and symptoms at the final level. This results in a top layer which is always linked to the critical clinical outcomes.

Figure 2:
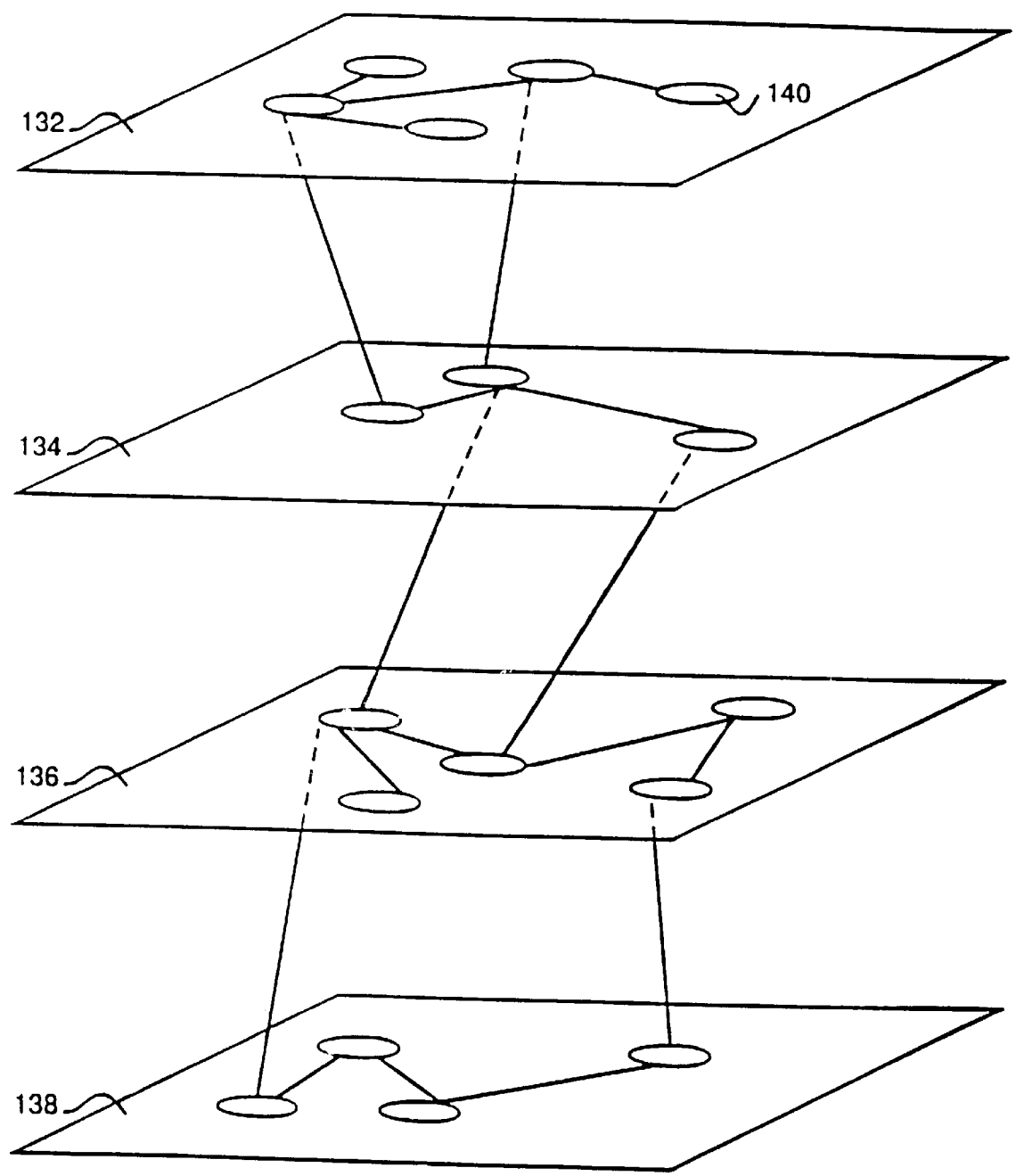
FIG. 2 is a block diagram showing linked fundamental model units on levels, and linking of fundamental model units between levels.

FIG. 2 is a block diagram showing linked Fundamental Model Units (FMUs) 140 on levels 132, 134, 136 and 138, and linking of FMUs 140 between levels. The lines linking FMUs 140 on and between levels 132, 134, 136 and 138 represent relationships between the individual entities. While FIG. 2 shows four levels, it should be kept in mind that a model may be comprised of one or more levels, depending on the complexity of the system being modelled. Typically, the model will consist of three or more levels, but a one or two-level model is certainly possible.

FIG. 3 is a block diagram showing a typical display and structure 68 of the entities making up the highest level of the model. This particular example level comprises Patient 56, Site A Surface 58, Bacteria A 52, Bacteria B 54, Site A Inflammation 60, Output 62, Attachment Site 64, and Clinical Observables 66. It should be kept in mind that the drawings in the present specification only convey information regarding making and using a hierarchical biological model, and are not intended to be biologically precise.

A typical entity on a level may be comprised of one or more inputs, a graphic element representing synthesis of those inputs, and one or more outputs. An entity may also have only one or more outputs or one or more inputs. Taking Bacteria A 52 as an example, the inputs are represented by the vertical blocks to the left of the double circles, the double circle graphic represents synthesis of the inputs, and the vertical blocks on the right represent outputs of the synthesis.

The information on display 68 is interactive in that a user is able to alter not only the particular elements shown, but can also modify the underlying information which the elements represent. For example, if the user were to select and open the double circles file representing Bacteria A 52, a lower level representation of the model would pop up on the screen, allowing the user to examine more detail about how the synthesis represented by the double circle graphic is accomplished. The physical appearance of the graphics representing synthesis from inputs to outputs can be customized by the user to convey meaning regarding the particular synthesis being performed and represented by the graphic. The synthesis may, for example, be a mathematical manipulation of the data input to the block.

Attachment Site A 64 shows several functional blocks attached to form a larger entity 64. Note also that some of the outputs on this level are also inputs on this level. For example, Allergy hx output from Patient 56 is an input in Attachment Site A 64. This internal interaction is a feature of biological systems which makes an understanding of a single entity only of limited use. The present invention combines these entities to create a complete model of the biological system.

Output block 62 provides for visual output of the variables which are input. This provides a user with the ability to grab various inputs or outputs and display them together in graph form, or in some other meaningful way which conveys the relationship among the data.

It should be kept in mind that while each numbered entity could be considered an FMU, an FMU could be comprised of a group of such entities. The phrase "Fundamental Model Unit" is only intended to be a convenient terminology for referring to entities making up the model.

Figure 4:
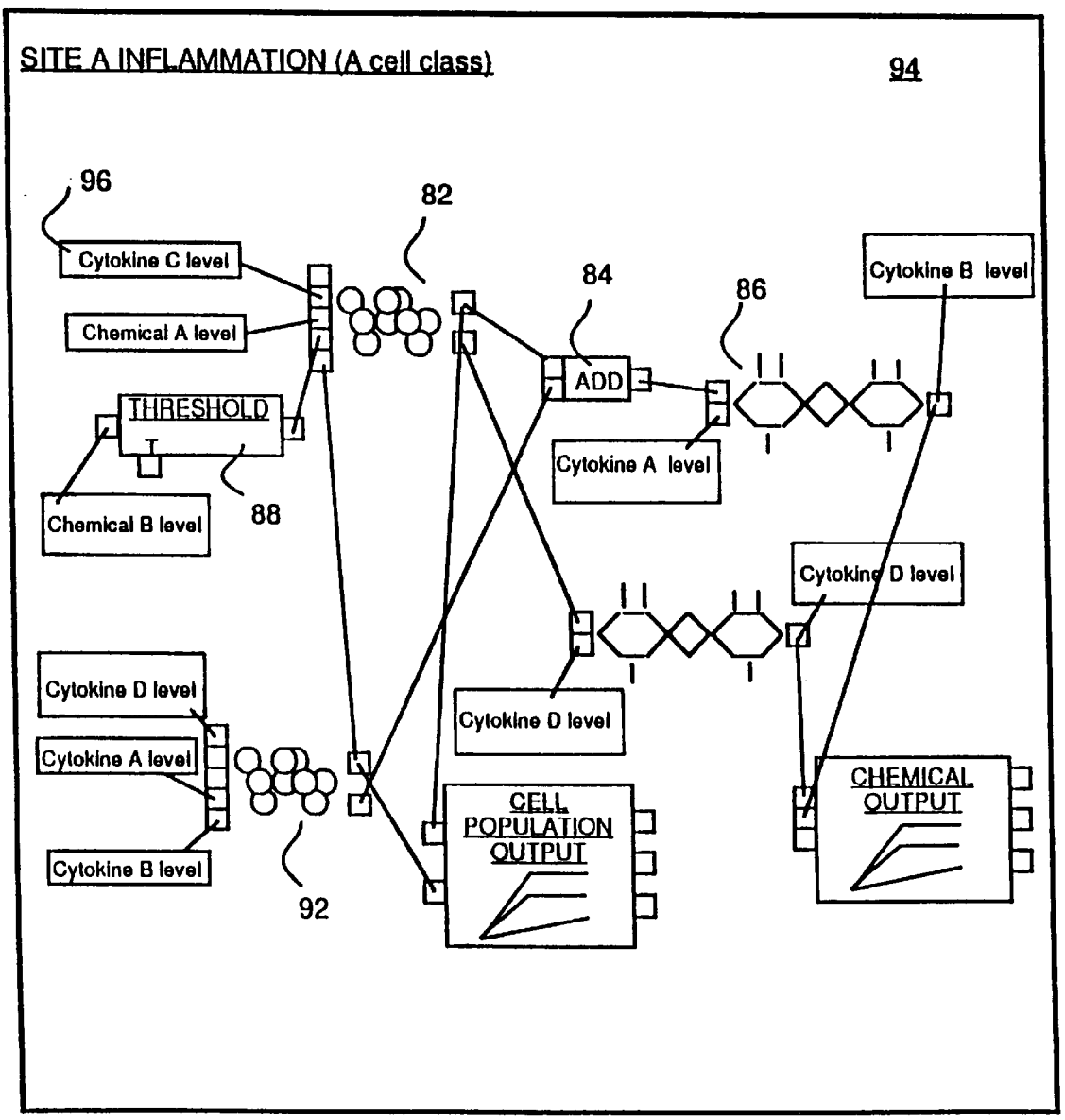
FIG. 4 is a block diagram showing what could be considered an interactive display and structure of a middle level of the hierarchy.

FIG. 4 is a block diagram showing an interactive display and structure 94 of the level of the hierarchy below the level shown in FIG. 3. This particular example shows an entity which represents the Site A Inflammation 60. This level could be comprised of a variety of entities such as Cell Poll Controllers 82, ADD Function Block 84, Chemical Production 86, Threshold Block 88, and Cell Pool Controllers 92. The general structure demonstrated by this level is that of Cell Class taking chemical inputs developed from a variety of sources, and outputting chemical levels produced by the various cell types. As discussed with respect to FIG. 3, FIG. 4 represents interactive graphics entities, as well as the overall biology of the level. Each of the graphical entities 82, 84, 86, 88 and 92 represent a synthesis of the respective inputs to each entity. The "boxed" inputs, such as that represented by 96, are data paths connected to data developed from another level.

Figure 5:
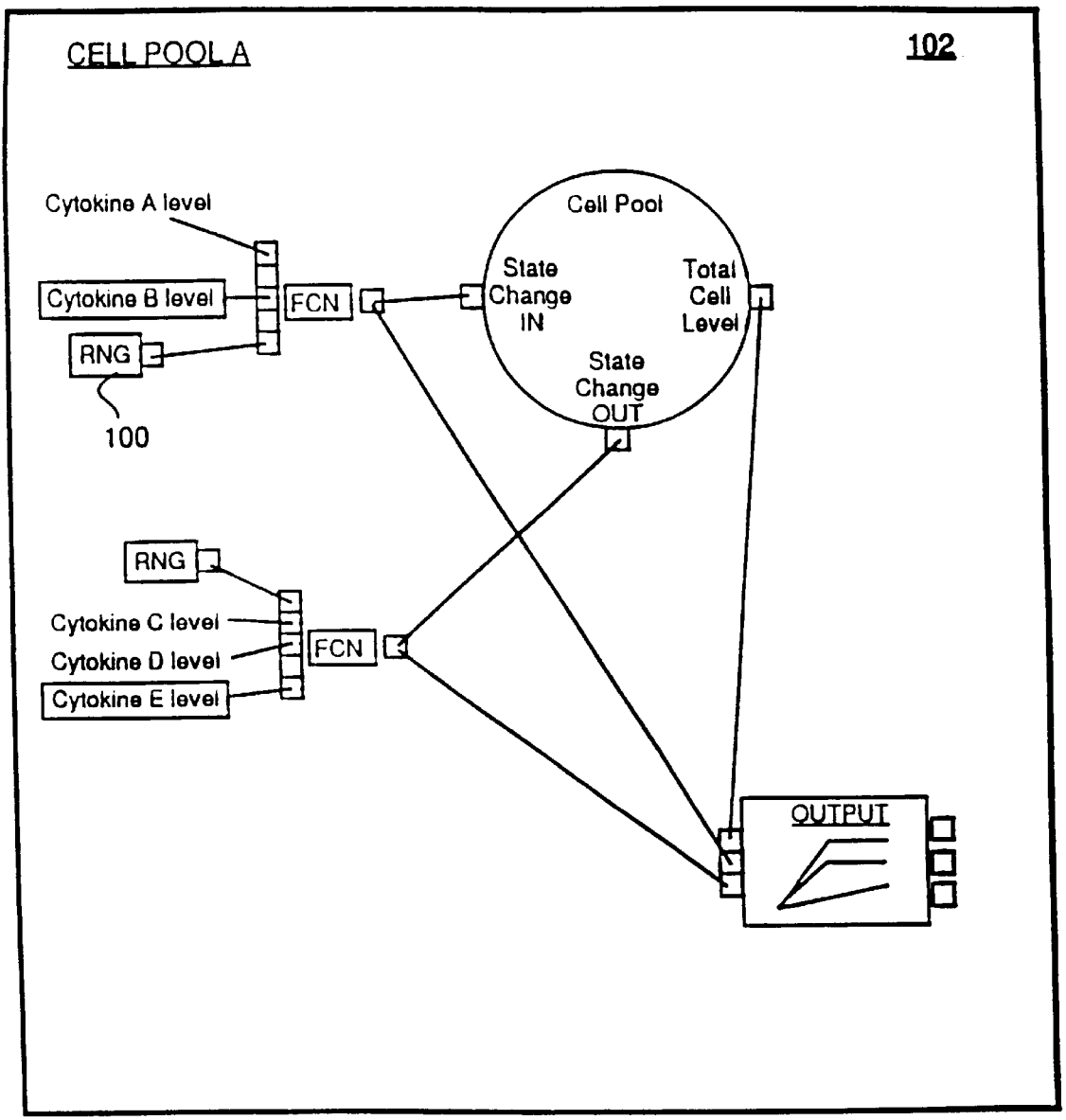
FIG. 5 is an example of an interactive display and structure of another level of the model hierarchy.

FIG. 5 is an example of an interactive display and structure 102 of another level of the hierarchy of a cell pool.. The use of Random Number Generators 100 provide a means for generating some of the material variation within the model that is found in biological systems. Such variation can support statistical analysis over a population when the model is run many times.

The model is capable of integrating complex interactions over time, which clarifies negative and positive feedback mechanisms that are critical to the homeostasis of an organism. Without the temporal integration it is not possible to identify the true regulatory nature of biological interactions.

DEVELOPMENT OF PURPOSE FOR A MODEL

The initial impetus for model development arises from recognition of a particular problem to be solved in the drug development field. A client may specify the particular disease aspect to model, such as the need to identify a new target for drug development or the need to design a clinical trial for an existing drug. From this information a determination may be made as to which building blocks must be included. For example, a client may wish to identify whether a specific input of an individual's biology is linked to a genetic variation. In this situation, the model is developed to include the biology to a level of detail necessary to link the variations in clinical outcomes to the variation in a patient's basic biology. As a result of this linkage, the cause of the biological variation can potentially be traced from the biological variation back to a specific genetic variation.

IDENTIFICATION OF RELEVANT FACTORS

After the problem has been identified, factors relevant to resolution of the problem are determined. For example, the particular "target patient" will have certain factors of high relevance which need to be explored in order to better understand the problem facing the target patient. Alternatively, perhaps certain observable factors regarding a drug or disease may reveal factors which need to be explored.

General information regarding the larger issues to be dealt with are then researched and discussed. This discussion may include, but is not limited to, disease experts, clinicians, regulatory experts, marketing, management, etc.

Figure 6:
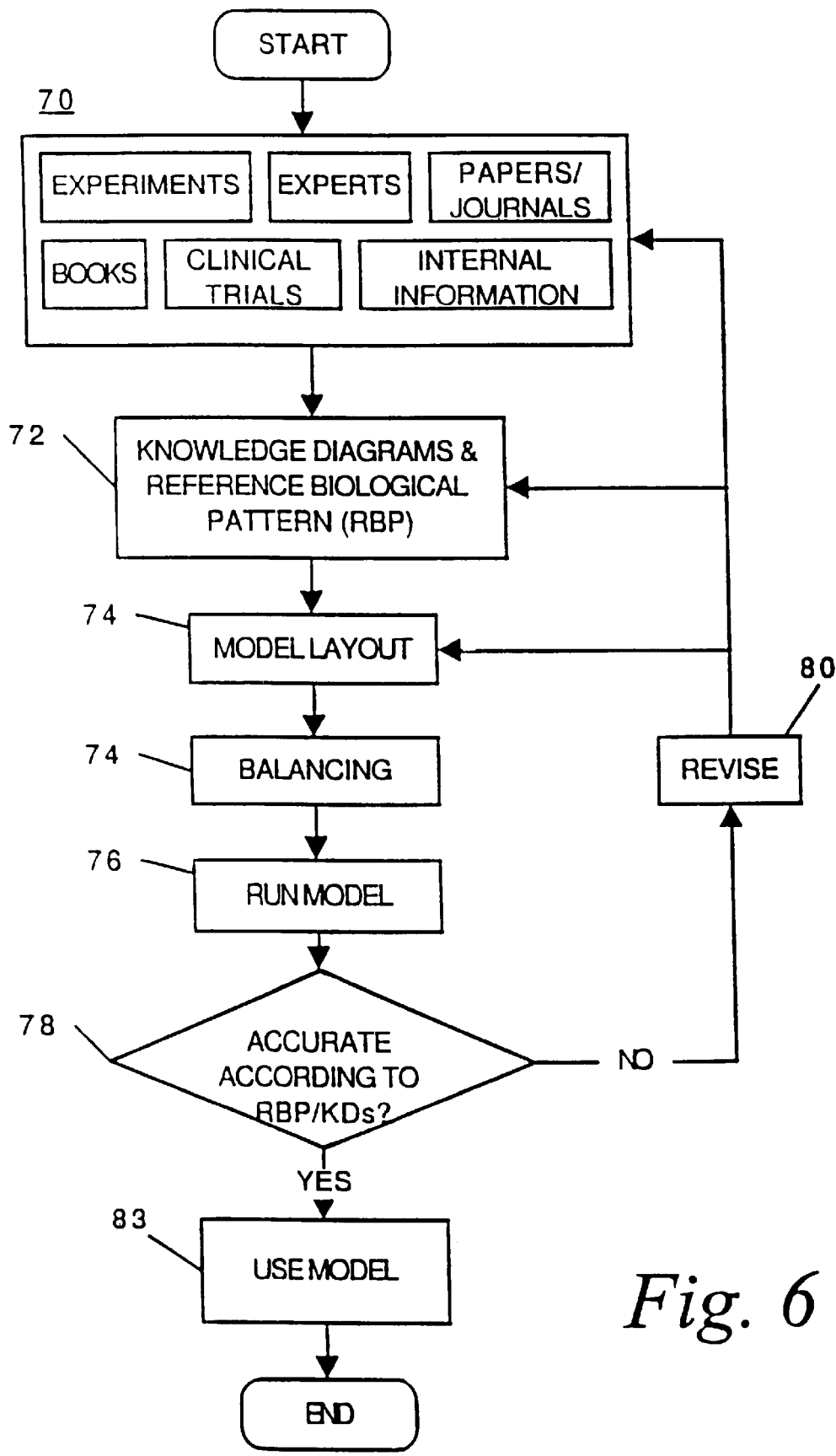
FIG. 6 shows the overall flow of operations for collecting information, developing a representation of the system, making a model, running the model and using the model.

FIG. 6 shows the overall flow of operations for collecting information, developing a representation of the system, building the model, and running the model. As indicated by 70, the first step of the process involves collecting information from a variety of sources, such as papers/journals, books, experts, experiments, clinical trials, and information developed internally to a company. From this information, a Reference Biological Pattern (RBP) is developed and Knowledge Diagrams (KDs) are constructed (72) to represent the collected knowledge. From the RBP and KDs, the interactive model is laid out (74) using the modelling tool and balanced (75) so that model behavior at all levels makes sense. Then the model is run (76), checked for accuracy against the RBPs and KDs (78), and revised (80), if necessary. Once the model is determined to be acurate it is ready for use (83).

If the model does check accurately against the RBP and KDs the model can be used to generate data that address the question posed at the beginning of the project. The model can be used for a variety of purposes, including drug development and clinical trial development.

CREATION OF THE REFERENCE BIOLOGICAL PATTERN AND KNOWLEDGE DIAGRAMS

The goal in creating the Reference Biological Pattern and Knowledge Diagrams is to define clinical outcomes of interest, the biological systems involved, and the relevant communication mechanisms between biological systems. The way the relevant biological factors behave over time and what therapies have been previously tried is also determined.

A RBP is based upon carefully selected experimental, often clinical, data showing what happens in real world situations. When the model is completed, it must gives outcomes matching the RBPs. This grounds the model in the reality of clinically observable outcomes. For example, if a patient has a middle ear infection, certain biological responses should be evident and certain clinical symptoms should be manifested, such as pain, bulging of the eardrum, etc. If the model does not duplicate real life outcomes in the range of interest, then it is not valid and requires modification.

The information gleaned from literature, books, experiments, internally developed information, and experts is synthesized into the "Knowledge Diagram". The KD captures the many relationships evidenced in the disparate sources of information. The KDs are representations of the relevant biological systems and processes and the relationships between them that must be built into the model.

KDs are constructed from elements connected by flow arrows. The flow arrows may have regulator indicators, such as plus and minus, which influence the flow represented by the flow arrow. The KDs incorporate many levels. The top level defines the disease, focusing on the clinical outcomes, biologic factors, and susceptibility factors. These are grouped into major functional units.

A next level defines in greater detail the key aspects associated with the disease. This level conveys what biological mechanisms are responsible for the top level aspects, what initiates the mechanisms, what controls and regulates the mechanisms, what inputs and outputs define the system, and what anatomic considerations are involved.

Figure 7:
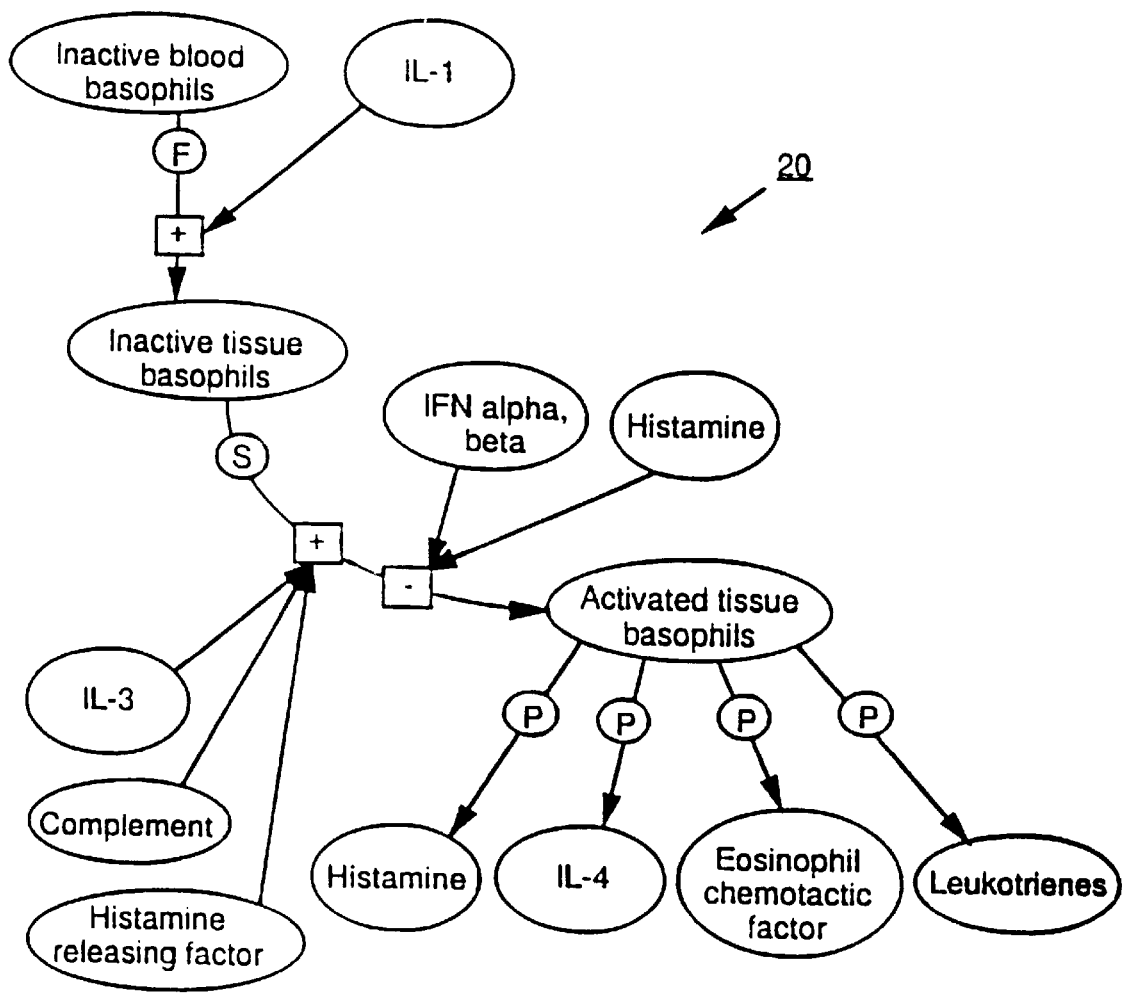
FIG. 7 shows an example of a knowledge diagram.

FIG. 7 shows an example of a Knowledge Diagram represented by numeral 20. The KD is intended to be an example only, and not biologically or medically accurate. In general, the diagram shows nodes representing entities and arcs representing interactions/relationships between the entities. The boxes having "+" and "−" therein indicate enhancing or inhibiting the particular interaction shown. This particular KD represents the activation process of the basophil cell. The arrows between cell types represents a flow or state change that is regulated positively and negatively..

CREATION OF THE MODEL

The model is then created based on the RBP and KDs. Nodes in the KDs labelled as cell types become cell pools in the model. Connections between cell pools in the model are based on state change links in the KD. These connections provide pathways for the flow of cells from one cell pool, representing one cell type/state, to another.

Connections between cell pools are "regulated," e.g., the number of cells selected for movement from one cell type/state to another, by the links that connect to the "+" and "−" boxes on the links between the cell pools. These controlling items usually designate chemical levels that either enhance or inhibit the cell transition between states. Each contributor to the transition function, or regulator, is weighted, usually with a value between 0 and 1. The sum of the weights of all contributors to a regulator usually totals 1. Initially, the weight for each chemical influencing a transition is assigned equally. These weights are then adjusted when the model is balanced. The calculation for a regulator is performed using a synthesis block. The result is a regulator that represents a percentage of the cells that should make the transition, and is used as a multiplier on the contents of a cell pool.

Based on the knowledge diagrams, the various cell types produce a variety of chemicals. Production of these chemicals is accomplished in the model primarily by a synthesis block. The input to the synthesis block is the quantity of cells of the type producing the chemical, along with the values of the various other chemicals that influence production of the particular chemical by the particular cell type. These chemical influences are weighted as they are in the cell transition links and must then be balanced. The chemical influences serve, as they do with the cell transition links, as regulators on the production of the chemicals, enhancing or inhibiting production as appropriate.

Cell pool types and the regulators associated with the cell pool types are combined into a higher level called a cell pool controller. Sets of related cell pool controllers are combined to form "cell classes." Cell classes can then be combined to form larger functions, such as the immune response or bone remodelling.

The Fundamental Model Unit

The general structure of a particular level is a collection of fundamental model units. These may be stand-alone model units, which serve to communicate information to, or receive and synthesize information from, another level. FMUs on a particular level may also be connected to other FMUs at that level, or connected to both other FMUs on the same level and FMUs on other levels.

An FMU can be thought of as a collection of inputs which are synthesized into one or more outputs. Examples of typical FMUs are cell classes, cell pool controllers, cell pools and regulators of cell pools.

The inputs may be comprised of virtually any item of information relevant to the biology of interest. These include items directly traceable to the biology, as well as items necessary to accurately convey information regarding the biological items. For example, a quantity of interleukin-1B may be a relevant biological factor at a particular cell site.

As discussed previously, randomness is made a part of the model via random number generators (RNGs). Probability distributions are chosen as part of the model to closely reflect the underlying distribution of the biology being modelled at any particular point. A typical probability distribution would be that of a Bell curve. Randomness can be used to represent natural variance in cellular events such as cell proliferation and apoptosis.

The RNGs can be used at any level of the hierarchy to provide a distribution of a particular type of information. For example, the RNG could be used to produce multiple patients, multiple groups of patients, multiple types of cellular reactions, etc. By using an RNG, key variables within expected biological ranges, having an expected biological distribution, can be generated. This provides a model with much greater real world accuracy and allows investigators to explore potential variances.

Internally, to simulate the normal variation between patients with the same basic characteristics, a random number generator varies certain biological parameters within their normal biological ranges. Each time the model is run, even with the exact same parameters, the answer will be slightly different. Running the model many times will provide a normal variation in clinical response for a given patient type.

Probability distribution functions are used along with the random number generators to further refine models of these dynamic systems. Fuzzy logic is also used as part of the process of manipulating information. Many biological aspects are analogous to the analysis carried out by fuzzy logic. Fuzzy logic is an artificial intelligence technique used to handle situations where membership in a set is not completely defined but occurs within some variance level.

Feedback loops are also used to create systems providing an accurate representation of complex biological systems. For example, one may know A affects B, which affects C, and C affects A. But how does changing B affect A? By providing the feedback loops which handle these relationships in a multi-variable, simultaneous fashion, non-intuitive insights about diseases, therapies, and other system characteristics can be provided from the model.

The process, or processes, represented by an FMU, group of FMU levels, or series of levels will all have particular time constraints within which they must operate to be biologically correct. These time frames may be on the order of fractions of seconds, months, or even years. Recurrent otitis media, for example, has some cycles which happen over hours, and other cycles which happen over months. Subcellular interactions, on the other hand, may happen in a matter of seconds, or less. FMUs incorporate these time factors by using rates either in the form of an input to a FMU, or within the synthesis performed by the FMU.

Linking Fundamental Model Units on Each Level and Between Levels

As stated previously, the bottom level of a model will typically represent a cellular or subcellular level. At this level there is usually no identifiable anatomy, only cellular or subcellular entities. These are represented by classes of cells known to be associated with a specific disease.

The next level in the hierarchy may be a system or anatomic area which is the primary locality of cells represented at the bottom level, and the system or anatomy area affected by the disease under study. For example, this level may represent the immunological system or an organ, such as the liver.

Further levels may include the larger biology within which the system or anatomic area resides, for example, external patient characteristics, and a next level may be patient populations and characteristics.

Regardless of the level, each level is composed of a plurality of FMUs who's inputs and outputs are linked to simulate the actual interation within the biologic system being modelled. Similarly, the FMUs on separate levels are linked to simulate the complete biologic system.

Model Balancing

Once the model is created in the modelling tool, the model must be run (executed) and "balanced" to create the desired, appropriate behaviors. Balancing is performed at two levels, the cell population level and the overall model level, and is extremely time consuming and labor intensive. Balancing requires input and knowledge not available or representable in the Knowledge Diagrams because it is this knowledge that makes the model executable. The balancing process can help to pinpoint holes and inconsistencies in available scientific knowledge.

Before and after the model is run, or executed, each fundamental model unit, group of fundamental model units, level, group of levels, or abstractions crossing these boundaries must be checked against corresponding real world entities of information from the RBP, which includes the KDs. For example, a particular piece of literature may deal with a particular biological system which is self contained within a particular level of the model. This level entity may be checked for accuracy against the real world information disclosed in the literature as described in the KDs and RBPs.

Initial cell balancing requires the development of stable cell pools when the model is run for each cell class, wherein the cell pools are at appropriate levels for the given conditions. Thus, under non-inflammatory conditions the cell classes must behave in a stable, healthy manner when the model is executed, while under increasingly challenging conditions they must either increase or decrease their numbers as appropriate and stabilize on a reasonable population count, or "set point." Each cell class must be balanced so that the interrelationships between the various cell controllers within a cell class perform properly and the cell pool populations achieve appropriate relative counts. A reasonable behavior for each cell population must first be obtained because all of the cell populations interrelate and have feedback among the cell populations. Once appropriate cell population behaviors are achieved for a cell class, the chemical production by the cell population is also balanced and normalized so that feedback is appropriate for the given condition.

With balanced, well-behaved cell classes, the next step is to establish an appropriately behaved overall model. This involves evaluating the interactions between cell classes through the chemicals that they produce when the model is run. Based on the behavior of the overall model when executed, each cell class is re-evaluated and re-balanced so that the interrelationships generate an overall global behavior that matches the clinical baselines, or RBPs, that have been developed. This helps to test and validate the model behavior under a variety of conditions.

As each cell class is re-balanced in the context of the whole model, the overall model is re-examined and adjusted for balance. Often, a cell class, already balanced, may need to be revisited and re-balanced, based on changes in another cell class and the chemicals it generates. This process of cell and model balancing is a highly iterative process that builds reasonable global model behavior through the development of appropriate behavior at the lowest levels in the model, the cell pools, on up through the cell controllers and the cell classes.

For example, the model of a healthy system may be run and modified until a balanced and stabilized system is achieved. A stable state is achieved when the results at each level and point are consistent with the RBP and Knowledge Diagrams. Chemical reaction rates, cell population growth, cell population diminishment, and barrier crossing rates are examples of a few of many Fundamental Model Units, or collections of Fundamental Model Units, which must be consistent with the RBP and Knowledge Diagrams.

Once the model is stabilized, a particular system may be introduced into the model, and the model is rebalanced to ensure that the model with the newly introduced system behaves consistent with the real world. For example, a "healthy" model representing components typical of a non-inflamed state could first be built and balanced. The system would be made of components relevant to the inflammatory system but operating in a healthy, noninflammatory manner.

Once the model appears to exhibit reasonable behavior under a variety of health and disease conditions, the values of the biologic outputs are re-interpreted and mapped into values that correlate with actual clinical outcomes. For example, a number between 0 and 100 indicating inflammation in submucosal tissue is mapped to an appropriate dimensional change in swelling of the tissue. The model is then systematically run and tested using a set of matrices on which cell population counts and chemical levels are recorded, along with the input values that define the patient data disease level, and possible therapies. The model is run repeatedly, systematically altering the various input data and recording the various internal outputs of the model, to ensure that not only the clinical outcomes of the model make sense, but the outcomes achieved through cell population and chemical production changes make sense as well. A redesign and/or a re-balancing of certain portions of the model may need to be made at this point to ensure proper behavior under the various key situations of interest.

Once the model has generated satisfactory behavior under a variety of healthy, diseased, treatment, and patient biologies, it can be delivered to the targeted users for examination by experts. These individuals do further testing and validating, by varying additional input parameters, but usually only checking the clinical outcomes of the model as opposed to all of the various cell populations and chemical levels. As a result of this testing, recommendations are made for final modifications to the model. These modifications are made, when possible and desirable, and the model is ready for use.

It is also contemplated that the model could be self-balanced by incorporating the RBP and KD into a data structure. The data structure would be referenced by the model after running and checking the model outputs against the expected acceptable results indicated in the RBP and KD data structures.

MODEL MAINTENANCE

The model should be maintained to reflect the most up-to-date information available on a particular system. If a new journal article indicates information which may alter the previous model, the model can be updated to incorporate these concepts.

CONNECTED MODELS

Figure 8:
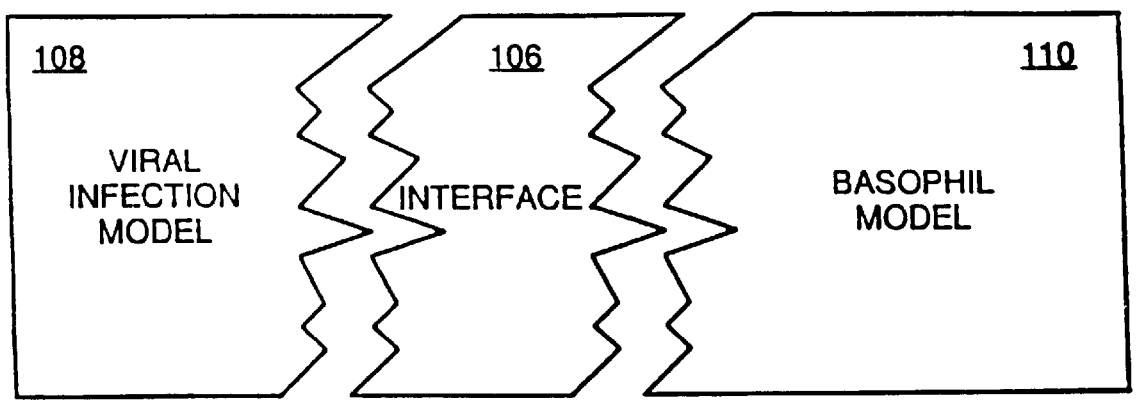
FIG. 8 shows an example of linking together two models.

FIG. 8 shows an example of linking together two models. In the particular example shown, a Viral Infection Model 108 is linked to a Basophil Model 110. The jagged edge on each of the two models represents the changing and synthesizing of information common to the two models, as well as the particulars of the overall system which are desired to be studied. The process for developing the interface 106 to allow the two models to work together is similar to that outlined above for creation of a single model. The general overall structure of each respective model is kept intact, but the models are merged through the creation of what could be considered an interface between the two models. The interface 106 is essentially a model of the interaction between the two models which are being connected. In the present example, the interface 106 would be a model of the viral infection/Basophil interface. While the interface 106 of FIG. 8 is shown as a separate element, it should be kept in mind that this is merely representative. In actuality, any entities between models which are related in some way may need to be altered to allow for the two models to work together. Thus, interface 106 represents changes on a FMU and level basis, as well as creation of new FMUs and levels to merge the two models.

Examples of linked models could include, but are not limited to, models of physical entities linked with models of other physical entities, models of physical entities linked with models of biological systems, and models of biological systems linked with models of other biological systems

MODEL USES

Drug Development

The model provides a means of collecting into a dynamic executable format information regarding drug impact at molecular, and other levels, to predict what will happen at the patient level. Drug treatment is input into the model in terms of the impact on certain biological factors. For example, an antimicrobial could be described in the model as a means of decreasing bacterial load 30%. The model is then executed and the effects this antimicrobial has on the immune system response, which can in turn influence certain organ responses can be reviewed. These organ responses may cause certain symptoms to remain or disappear.

As a second example, consider a drug such as ibuprofen which reduces prostaglandin levels and in turn impacts a variety of inflammatory responses in the model. The lowered level of prostaglandin production is simulated by the model, and the model when executed determines the effect on the other key systems, ultimately outputting the effect of lower prostaglandin levels at the patient level. From this information regarding lowered levels of prostaglandin, valuable information about drug behavior and effect may be observed and discovered. The information may include typical values, or ranges, of pharmacological effects, pharmacokinetics for timing and dose implications, human clinical experience, etc. These are all very helpful in identifying drugs for a particular disease.

The present invention may be used to assist in the identification and early assessment of potential targets for new drug development by allowing scientists using the model to explore within a more complete system from which observations and hypotheses can be made, based on knowledge of the subcellular and cellular levels and their effects on clinical outcomes. The model can identify biologic factors that have the greatest leverage on clinical outcomes in the particular disease.

Clinical Trial

The model can be run using various patient and treatment characteristics to determine the patients that would benefit most from specific treatments and those patients that may experience problems in the study. This would provide optimal patient selection and appropriate design factors to detect, monitor or handle any negative outcomes.

The model can also evaluate different time lengths for clinical trials, optimal times to take clinical measures, and even the dosing schedule for the drug. Since it can simulate trial results for any combinations, different clinical trial options can be run.

A user can stipulate the characteristics of an individual patient, or those characteristics that typify a particular group of patients. For example, is the patient a smoker, is there a family history of certain disease, is the patient compromised with other systemic conditions that effect outcomes, etc. Then the drug or treatment regimen is input. The model is run and the output is the clinical status or clinical result from applying that treatment to that patient or patients.

HUMAN INTERFACE

The human interface of the model provides the user an input to and an output from the model. The graphics interface can be customized to reflect the particular application for which a model is being used. Other typical human interface elements, such as keyboards, a mouse, trackballs, touchscreens, printers, etc. can also be used.

COMPUTER SYSTEM

Figure 9:
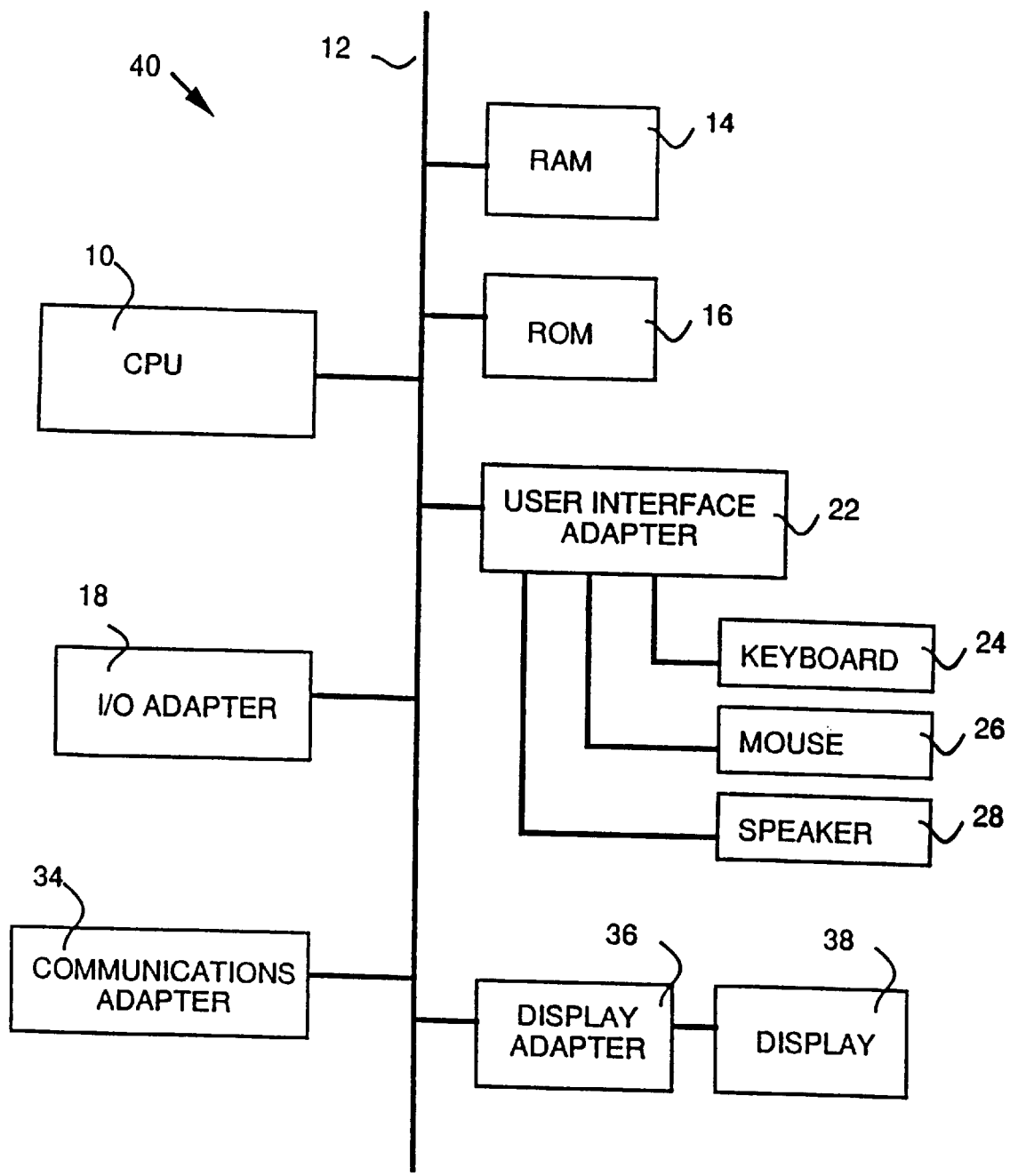
FIG. 9 represents a computer system on which the present invention may be practiced.

FIG. 9 represents a computer system 40 on which the present invention may be practiced. The computer system includes a CPU 10, I/O Adapter 18, Communications Adapter 34, RAM 14, ROM 16, User Interface Adapter 22 having connected thereto a Keyboard 24, Mouse 26, and Speaker 28, a Display Adapter 36, and Display 38. All elements are connected to Bus 12. The computer system shown is merely exemplary, and is not intended to be limiting. The computer system could be of virtually any size or power, depending on the particular complexities of the model.

While the invention has been described in terms of a preferred embodiment in a specific system environment, those skilled in the art recognize that the invention can be practiced, with modification, in other and different hardware and software environments within the spirit and scope of the appended claims.

I claim:

1. A computer executable model of a hierarchical biological system, the model for use with a computer system including a memory and a processor, the model comprising:
a plurality of biological modelling units stored in the memory, each biological modelling unit having:
a plurality of chemical level inputs, each input representing a level of a chemical in an environment containing the biological modelling unit;
at least one chemical production output representing a level of a chemical produced by the biological modelling unit and stored as part of the environment containing the biological modelling unit; and
a chemical production function describing the production output of a chemical by the biological modelling unit as a function of the chemical level inputs; and
the plurality of biological modelling units organized into a plurality of levels, each level representing a different level of biological function, each biological modelling unit in any level providing its chemical production outputs to the environment containing the biological modelling unit, receiving as its chemical level input, chemical levels from the environment, and wherein execution of the model by the processor modifies the respective inputs and outputs of each of the biological modelling units.

2. The computer executable model of claim 1, further comprising:
a regulator biological modelling unit representing a regulator function comprising:
at least one chemical level input representing a level of a chemical in an environment containing the regulator biological modelling unit;
at least one quantity input representing a quantity of a first type of biological modelling unit in the environment; and
a regulator function describing a change in state of the first type of biological modelling unit to a second type of biological modelling unit as a function of the chemical level and quantity inputs, wherein execution of the model by the processor causes respective changes in the quantities of the first and second types of biological modelling units.

3. The computer executable model of claim 1, wherein first and second biological modelling units represent first and second cell pools, each cell pool representing cells of a particular type or cells in particular state, the model further comprising:
a regulator biological modelling unit representing a regulator function comprising:
at least one chemical level input representing a level of a chemical in an environment containing the regulator biological modelling unit;
at least one quantity input representing a quantity of a first type of biological modelling unit in the environment; and
regulator function describing a change in state of the first type of biological modelling unit to a second type of biological modelling unit as a function of the chemical level and quantity inputs, wherein execution of the model by the processor causes respective changes in the quantities of the first and second types of biological modelling units, and representing changes in the quantities of cells in the respective first and second cell pools.

4. A computer executable model of a hierarchical biological system, the model for use with a computer system including a memory and a processor, the model comprising:
a plurality of cell pool modelling units stored in the memory, each cell pool modelling unit representing a quantity of a cells having a particular cell type or a particular cell state, each cell type modelling unit having:

at least one chemical level input representing a level of a chemical in an environment containing the cell pool modelling unit;

at least one quantity input representing a quantity of a cells of a selected cell pool modelling unit; and at least one chemical production function, executable by the processor, that outputs a level of a chemical produced by the cell pool modelling unit in response to the chemical level input and quantity input;

wherein execution of the model by the processor causes the chemical production function of each cell pool modelling unit to modify the output of the level of chemical of produced by the cell pool modelling unit; and a plurality of regulator modelling units stored in the memory, each regulator modelling unit associated with selected first and second cell pool modelling units, and having:

at least one input of either:
 a level of a chemical in the environment of the first cell pool modelling unit; or
 a quantity of a cell in the environment of the first cell pool modelling unit; and a regulator function, executable by the processor, and representing the transition of cells between the first and second cell pool modelling units by modifying the quantity of the cells represented by the first cell pool modelling unit and the quantity of cells represented by the second cell pool modelling unit; and wherein execution of the model by the processor causes each regulation function to dynamically modify the quantity of cells represented by each cell pool modelling unit.

5. A computer executable model of a hierarchical biological system, the model for use with a computer system including a memory and a processor, the model comprising:

a plurality of cell pool modelling units stored in the memory, each cell pool modelling unit representing a quantity of cells of a particular type of cell or a particular cell state and having a chemical production function describing an output level of a chemical produced by the cells of the cell pool modelling unit as a function of either a quantity of cells of at least one cell pool modelling or a level of a chemical;

a plurality of cell pool regulator functions, stored in the memory and executable by the processor, each cell pool regulator function regulating the quantities of cells associated with selected ones of the cell pool modelling units in response to inputs including at least one of a level of a chemical in an environment containing the cell pool modelling units or a quantity of cells represented by a cell pool modelling unit;

a plurality of a cell class modelling units stored in the memory, each cell class modelling unit associated with selected ones of the cell pool modelling units and selected ones of the cell pool regulator functions, and representing the biological functions of a single class of cells;

a plurality of system modelling units stored in the memory, each system modelling unit associated with selected ones of the cell class modelling units, and representing a coordinated biological function of an anatomic system; and wherein execution of the model causes the chemical production functions of the cell pool modelling units to dynamically modify the levels of chemical produced by the cell pool modelling units, and causes the cell pool regulator functions to dynamically modify the quantities of cells represented by the cell pool modelling units.

* * * * *

UNITED STATES PATENT AND TRADEMARK OFFICE
Certificate

Patent No. 5,808,918                                                        Patented: September 15, 1998

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Pamela K. Fink, San Antonio, TX; Kenneth S. Kornman, San Antonio, TX; Samuel Holtzman, Cupertino, CA; and Thomas S. Paterson, Woodside, CA.

Signed and Sealed this Twenty-Eighth Day of December, 1999.

KEVIN TESKA, *SPE*
Art Unit 2763

REEXAMINATION CERTIFICATE (4606th)

United States Patent
Fink et al.

(10) Number: US 5,808,918 C1
(45) Certificate Issued: Jun. 25, 2002

(54) HIERARCHICAL BIOLOGICAL MODELLING SYSTEM AND METHOD

(75) Inventors: Pamela K. Fink; Kenneth S. Kornman, both of San Antonio, TX (US); Samuel Holtzman, Cupertino; Thomas S. Paterson, Woodside, both of CA (US)

(73) Assignees: Interleukin Genetics, Inc., San Antonio, TX (US); Entelos, Inc., Menlo Park, CA (US)

Reexamination Request:
No. 90/005,700, Apr. 5, 2000

Reexamination Certificate for:
Patent No.: 5,808,918
Issued: Sep. 15, 1998
Appl. No.: 08/882,597
Filed: Jun. 25, 1997

Certificate of Correction issued Dec. 28, 1999.

Related U.S. Application Data

(63) Continuation of application No. 08/422,175, filed on Apr. 14, 1995, now Pat. No. 5,657,255.

(51) Int. Cl.[7] .................................................. G06G 7/48
(52) U.S. Cl. ............................... 703/11; 703/6; 702/19; 702/21
(58) Field of Search ....................................... 703/11, 12

(56) References Cited

PUBLICATIONS

Douglas S. Riggs, M.D., *Control Theory and Physiological Feedback Mechanisms*, The Williams and Wilkins Co. Eds., (1970).

Douglas S. Riggs, M.D., Macula Densa Chloride, Angiotension II, Glomerular Filtration Rate. (A Preliminary Hypothesis), *Control Theory and Physiological Feedback Mechanisms*, The Williams and Wilkins Co. Eds., 457–460 (1970).

Computer Simulation in Cancer Research (Chapter 7), *Structuring Biological Systems—A Computer Modeling Approach*, S. Sitharama Iyengar, Ph.D., ed., 210–226 (1992).

Douglas S. Riggs, M.D., Inhibition Synthetic Pathway, *Control Theory and Physiological Feedback Mechanisms*, The Williams and Wilkins Co., Eds., 374–381 (1970).

Douglas S. Riggs, M.C., Acute Gouty Arthritis, *Control Theory and Physiological Feedback Mechanisms*, The Williams and Wilkins Co., Eds., 508–509 (1970).

Douglas S. Riggs, M.D., Acute Pulmonary Edema, *Control Theory and Physiological Feedback Mechanisms*, The Williams and Wilkins Co., Eds., 500–503 (1970).

*Primary Examiner*—Kyle J. Choi

(57) ABSTRACT

A hierarchical biological modelling system and method provides integrated levels of information synthesized from multiple sources. An executable model of a biological system is developed from information and structures based on the multiple sources. The model is balanced to ensure that it matches the information and structures. Once the model is created and balanced it can be used to provide insight into phenomena at the cellular, or subcellular level, as well as phenomena at the patient, organ and system levels. From this information clinical trials can be emulated, biologic targets for drug development can be identified and subcellular phenomena over time can be observed. The model provides an integrated view of a multi-variable biological system.

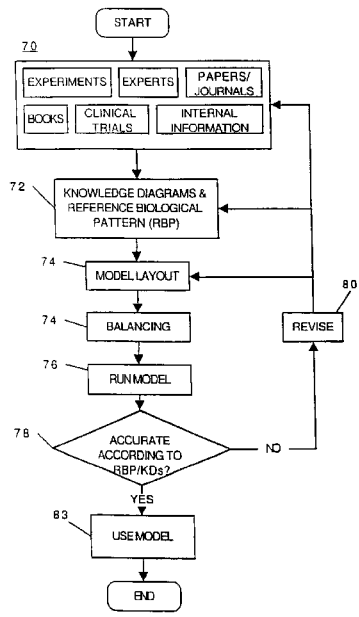

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–5 is confirmed.

\* \* \* \* \*